United States Patent [19]

Haugland

[11] Patent Number: 5,437,980
[45] Date of Patent: Aug. 1, 1995

[54] PHENANTHRIDIUM DYE STAINING OF NUCLEIC ACIDS IN LIVING CELLS

[75] Inventor: Richard P. Haugland, Eugene, Oreg.

[73] Assignee: Molecular Probes, Inc., Eugene, Oreg.

[21] Appl. No.: 63,870

[22] Filed: May 17, 1993

[51] Int. Cl.$^6$ .............................................. C12Q 1/68
[52] U.S. Cl. ....................................................... 435/6
[58] Field of Search .............................................. 435/6

[56] References Cited

U.S. PATENT DOCUMENTS 4,871,249  10/1989  Watson .................... 356/73
5,057,413  10/1991  Terstappen ................ 436/6

OTHER PUBLICATIONS

Jacquemin-Sablon, H. et al., Yeast mitochondrial deoxyribonuclease stimulated by ethidium bromide. III. Possible Involvement . . . , Mutation Res., (1980), 71:77–79.
Begg, A. C., et al., Cell Kinetic Analysis of Mixed Populations Using Three-Color Fluorescence Flow Cytometry, (1991), 12:445–454.
Haugland, Handbook of Fluorescent Probes and Research Chemicals, Set 31 (5th Ed. 1992, Molecular Probes, Inc., Eugene, Oreg.), pp. 221–229.
Tanke, et al., J. Immunol. Meth., 52,91 (1982).
Bucana, et al., J. Histochem. & Cytochem., 34, 1109 (1986).
Watkins, J. Chem. Soc., 3059 (1952).
Watkins & Wolf, Nature, 169, 506 (1952).
Walls, J. Chem. Soc., 294 (1945).
Brinkley, Bioconj. Chem., 3, 1–13 (1992).

Primary Examiner—Margaret Parr
Assistant Examiner—David Schreiber
Attorney, Agent, or Firm—Allegra J. Helfenstein; Anton E. Skaugset

[57] ABSTRACT

The invention relates to use of fluorescent compounds of the formula:

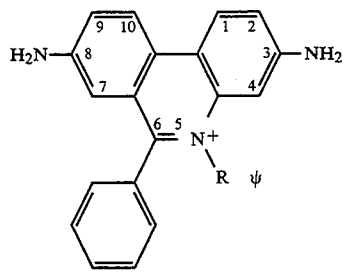

where R contains between 4 and about 10 carbons and is optionally saturated or unsaturated, and is linear or branched or contains an alicyclic or aromatic ring; and the symbol $\Psi$ depicts the presence of the counterion used to neutralize the positive charge on the dye. The fluorescent dye dissolved in a biologically compatible solution stains a wide variety of living cells with a red nucleic acid stain after brief incubation in low concentrations of dye, without the requirement of permeabilizing reagents. Detection of the fluorescence can be used alone or in combination with measurement of other markers or properties of the cells to identify, discriminate or sort viable cells.

20 Claims, 1 Drawing Sheet

PHENANTHRIDIUM DYE STAINING OF NUCLEIC ACIDS IN LIVING CELLS

FIELD OF THE INVENTION

The invention relates to a method of staining nucleic acids in living cells using phenanthridium dyes. In particular, the invention relates to 5-substituted derivatives of 3,8-diamino-6-phenylphenanthridium that are permanent to living cells under physiological conditions.

BACKGROUND INFORMATION

Fluorescent dyes are known to be particularly suitable for biological applications in which a highly sensitive detection method is desirable. By binding to a specific biological ingredient in a sample, a fluorescent dye can be used to indicate the presence or the quantity of the specific ingredient in a sample.

A variety of fluorescent dyes are commercially available for specific fluorescent staining and quantitation of DNA and RNA, and other applications involving nucleic acids, see e.g. Haugland, HANDBOOK OF FLUORESCENT PROBES AND RESEARCH CHEMICALS, Set 31 (5th Ed. 1992, Molecular Probes, Inc., Eugene, Oreg.) (incorporated by reference). Among these are derivatives of 5-substituted-3,8-diamino-6-phenylphenanthridium (5-DAPP):

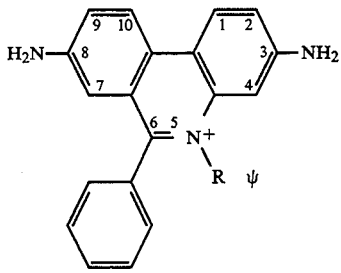

When R is ethyl, the dye is commonly called ethidium. When it is methyl, the dye is methidium. If R is 3-(N,N-diethyl-N-methylammonium)propyl, the dye is propidium. Various other analogs of 5-DAPP are known, including symmetric or asymmetric dimeric derivatives, derivatives in which the position(s) of the amino groups are changed or the amino groups are further modified by chemical substitution or omission and derivatives in which the aryl moiety is replaced by modified aryl, alkyl, arylalkyl or heteroaryl groups or by hydrogen.

Ethidium and its analogs were originally studied in the early 1940's as therapeutic agents for treatment of trypanosomiasis. They were subsequently found to bind to nucleic acids. This binding can be detected by the change in fluorescence properties of the nucleic acid complex following dye binding. When bound to nucleic acids, the 5-DAPP dyes generally have desirable fluorescence spectral properties. In particular, they absorb light at 488 nm and 514 nm, making them useful with instrumentation that uses the argon laser as an excitation source, such as flow cytometers and laser scanning microscopes. Furthermore, the fluorescence emission of the 5-DAPP dyes has a Stokes shift that is sufficient to permit detection of their fluorescence usually at a wavelength beyond about 580 nm, so that cellular autofluorescence is reduced. This characteristic also makes a 5-DAPP dye useful for multicolor applications in conjunction with a second dye, such as fluorescein or one of its conjugates, that is excited by the same source, but whose fluorescence is optimally detected at a shorter wavelength (typically at less than about 540 nm).

Not all nucleic acid stains can be used with living cells. To be useful for the analysis of nucleic acids in living cells, a detection reagent must be able to enter living cells and to respond to the presence of nucleic acids. It is particularly important to be able to stain nucleic acids in viable cells if it is desired to analyze and, if needed, sort viable cells according to the nucleic acid content or proliferative state of these cells based on their fluorescence. It is furthermore of importance to retain the cell viability if one wishes to sort and clone cells based on some additional fluorescence parameter.

It is generally recognized that ethidium and its analogs are usually not suitable for staining of nucleic acids in living cells in which the cell membrane is intact, except for permeabilized cells or at very high dye concentrations. Consequently several of these probes, in particular ethidium bromide (Tanke, et al., J. IMMUNOL. METH. 52, 91 (1982)), propidium iodide (U.S. Pat. No. 5,057,413 to Terstappen et al. Oct. 15, 1991 U.S. Pat. No. 5,314,805) and ethidium homodimer (Live/Dead ® kit, U.S. Ser. No. 07/783,182 to Haugland, et al., filed Oct. 26, 1991) U.S. Pat. No. 5,314,805, have been used extensively to detect and quantitate cells in which the membrane is compromised or missing, i.e. dead cells.

Making the 5-DAPP dyes more useful for staining nucleic acids in a wide variety of living cells requires improving access of the dyes to intracellular nucleic acids. Although numerous methods for enhancing permeability of organic compounds into cells have been described, including chemical- or electro-permeabilization, scrape loading, use of detergents, microinjection or various means of mechanical disruption, all of these methods intrinsically have the potential disadvantage of altering the properties of the cell membrane and thus the cell's intrinsic properties or proliferative capacity. Furthermore it is often difficult to achieve uniform labeling or reproducibility using these methods and some of the methods such as microinjection are not technically feasible on very small or fragile cells.

One method for improving the uptake of ethidium into living cells involves the chemical reduction of ethidium bromide to a dihydrophenanthridine derivative with no positive charge, see e.g. Bucana, et al., J. HISTOCHEM. & CYTOCHEM. 34, 1109 (1986). Unlike ethidium or the subject materials, this compound does not bind to nucleic acids and requires the secondary step of intracellular oxidation to regenerate ethidium intracellularly. Although the ultimate result in certain types of living cells is nuclear staining by a 5-DAPP derivative, not all cells are capable of oxidizing this type of dihydrophenanthridine to the nucleic acid stain.

This invention describes an effective means for improving uptake and staining of certain 3,8-diaminophenanthridium dyes in a wide variety of viable cells in culture or tissues by slightly increasing the size of the quaternizing substituent at the 5-position of the phenanthridine ring and thereby increasing the lipophilicity of the probe. Although only a slight chemical modification, this change significantly improves the permeability of the dye through the membrane of living cells and thus the staining of viable cells without significantly altering the ability of the dye to stain nucleic acids and without appreciably altering the spectral properties of the complex. There is an optimal size of the quaternizing substituent in that a further increase in size of the substituent has a deleterious effect on the nucleic acid staining by the dye. These reagents enable the staining of nucleic acids in living cells by a simple incubation with the reagent in standard culture medium, or in vivo by injection in a suitable biologically compatible fluid such as saline without resorting to use of harsh additives. Furthermore, use of these reagents permits detection, analysis and, if required, sorting of the viable cells based on the fluorescence intensity of their complex with nucleic acids, or based on fluorescence polarization, excited state fluorescence lifetime, or other dye-nucleic acid complex-related optical properties.

The subject dyes have the same basic 5-DAPP structure as does ethidium, except that instead of the two-carbon alkyl group as in ethidium, the substituent R at the 5-position of the phenanthridium ring contains 4 or more carbon atoms. Synthesis of a few examples of 5-DAPP molecules for use as drugs has been described in earlier publications, e.g. Watkins, J. CHEM SOC. 3059 (1952) (incorporated by reference). This paper and a related paper, Watkins & Woolfe, NATURE 169, 506 (1952) compare the use of various derivatives of 5-DAPP as trypanocides and conclude that the therapeutic potential of ethidium is superior to that of other 5-DAPP derivatives with longer alkyl chains. The Watkins paper speculates that the concentration of the free-base form of ethidium at pH 6–9 is greater than that of methidium (which is shown to be less effective than ethidium) and that this property may result in an increased rate of diffusion of the ethidium versus methidium across the cell membrane into the trypanosome cytoplasm. Watkins does not, however, indicate that other less effective 5-DAPP derivatives would diffuse across the cell membrane more quickly than ethidium or that they would be useful as fluorescent detection reagents for nucleic acids in living cells.

A application Ser. No. 08/047,683, abandoned (incorporated by reference) describes the use of the subject dyes to distinguish between live gram-positive and live gram-negative bacteria. Although dyes such as hexidium also lightly stain some gram negative organisms when used alone, the staining of gram-positive cells is significantly greater. This discrimination is not possible with ethidium, which does not effectively stain either live gram negative or live gram positive bacteria under the same mild conditions.

SUMMARY OF THE INVENTION, INCLUDING PREFERRED EMBODIMENTS

Figure 1:
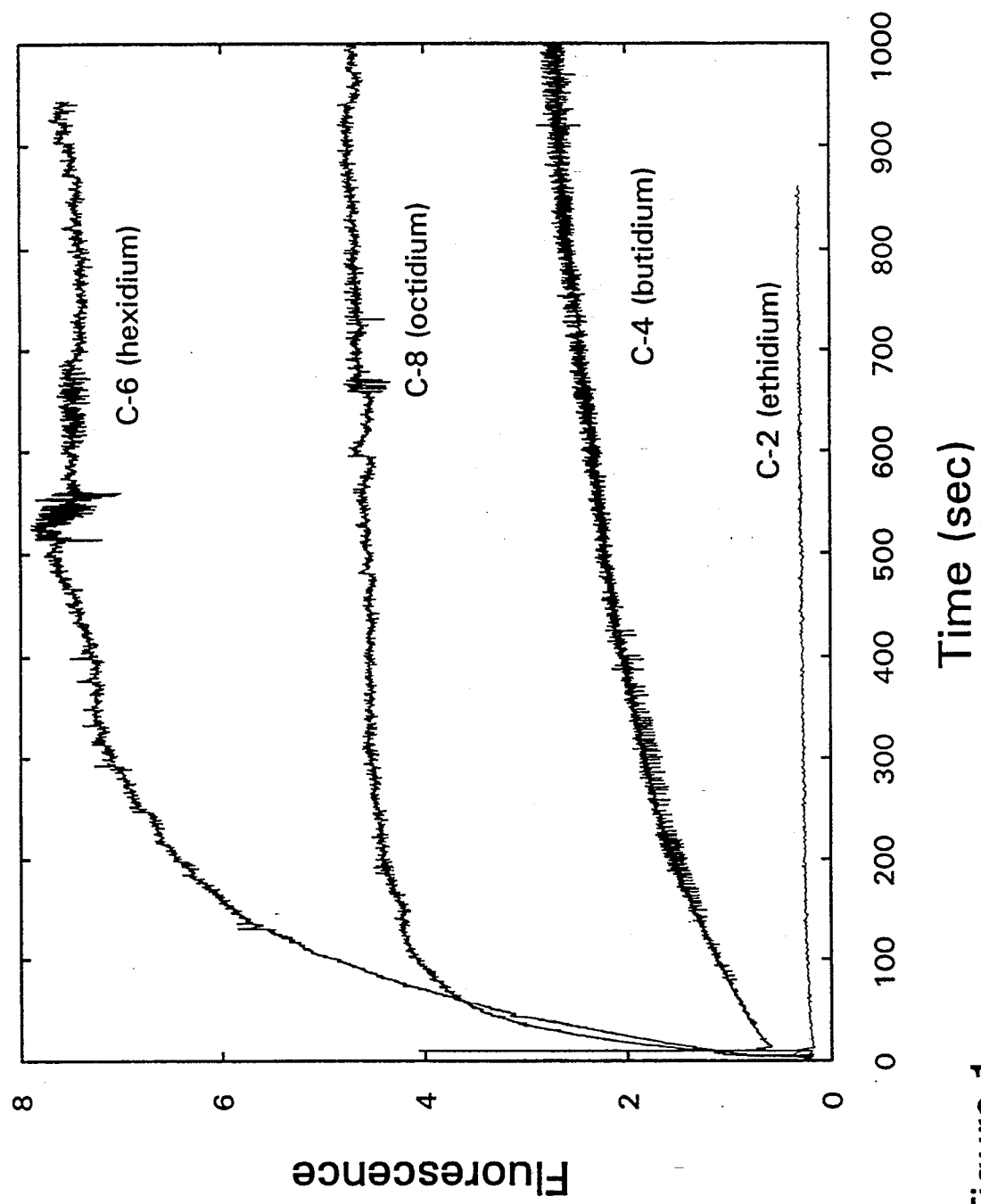
FIG. 1. Relative Uptake of Dyes into Living Cells. Uptake of ethidium, butidium, hexidium and octidium by *Bacillus cereus* as described in Example 2.

This invention describes a method of staining nucleic acids in living cells under physiological conditions with a dye that is excitable at about 488 nm and about 514 nm or in the range of about 480 to 520 nm and emits detectable fluorescence at a wavelength greater than about 540 nm.

The method involves the use of a biologically compatible staining solution comprising a dye of the formula (5-DAPP/LIVE):

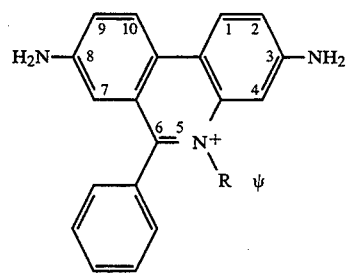

where the substituent R contains from 4 to about 10 carbons and the symbol $\Psi$ depicts the presence of the counterion used to neutralize the positive charge on the dye. Preferably R contains between 4 and 8 carbons and is optionally saturated or unsaturated, and is linear or branched or contains an alicyclic or aromatic ring. For example, R is a saturated or unsaturated butyl, pentyl, hexyl, heptyl or octyl substituent that is optionally branched, or R is phenalkyl or alkyl substituted phenalkyl, or R contains a cyclohexyl, cyclopentyl, cyclobutyl or cyclopropyl ring. When R is unsaturated it contains 1 to 4 carbon-carbon double or triple bonds in any combination. In one aspect of the invention, R contains less than about 11 carbons and contains a cyclic structure that is aromatic or alicyclic, such as a 6-membered ring. Preferably R is saturated n-butyl, n-pentyl, n-hexyl, n-heptyl or n-octyl, of which n-hexyl is preferred for most detection assays. When R is n-butyl, the dye is termed here "butidium"; when R is n-pentyl the dye is termed "pentidium"; when R is n-hexyl the dye is termed "hexidium"; when R is n-heptyl the dye is termed "heptidium"; when R is n-octyl the dye is termed "octidium"; and when R is phenethyl ($C_6H_5CH_2CH_2-$) the dye is termed "phenethidium."

Synthesis and characterization of butidium and hexidium is described in Watkins. This method is also generally useful for preparing compounds where the quaternizing substituent contains a cyclic structure. In general, the substituent R is incorporated into the 5-DAPP/LIVE reagent by reaction of a suitably amine-protected 3,8-diamino-6-phenylphenanthridine with an alkylating agent R—X wherein X is a "leaving group" that activates the alkyl portion of the reagent to nucleophilic displacement. Usually the protecting group is ethoxycarbonyl and R is the desired 5-DAPP/LIVE substituent, i.e. a saturated or unsaturated, linear or branched alkyl chain or contains an aromatic or alicyclic ring. Other amine-protecting groups such as carbobenzyloxy that prevent or reduce reaction of the alkylating reagent with the amines of the phenanthriduim are also suitable. Typically, the leaving group X from the alkylating agent provides the required counterion $\Psi$ for the dye, which is a halogen (preferably iodide or bromide) or a sulfonate ester (preferably p-toluenesulfonate, p-chlorobenzenesulfonate or trifluoromethanesulfonate). Other counterions $\Psi$ such as perchlorate, phosphate, sulfate, carbonate, bicarbonate, or tetrafluoroborate or anions of an organic carboxylic acid or sulfonic acid with less than about 8 carbon atoms are typically obtained by ion exchange subsequent to alkylation and deprotection.

Variants of 5-DAPP dyes in which the 6-phenyl moiety is further substituted or replaced by other aromatic, heteroaromatic, aliphatic substituents or in which the amino groups are modified or missing are known e.g.

Watkins, supra; Walls, J. CHEM SOC. 294 (1945). Equivalent versions of these prepared with the same R substituent from suitably protected intermediates enhances their membrane permeability. Usually these modified versions of the 5-DAPP dyes do not provide additional benefits and they usually require greater effort for their synthesis. Variations on methods for synthesis of the subject dyes or for incorporating additional non-carbon or non-hydrogen atoms into R or at other sites on the molecule are well documented in the literature or are obvious to one skilled in the art, and result in equivalent compounds.

The biologically compatible staining solution is made by dissolving the dye directly in an aqueous solvent such as water or tissue culture medium or buffer such as phosphate buffered saline, or, more commonly, by dissolution in an organic water-miscible solvent such as dimethylsulfoxide (DMSO), dimethylformamide (DMF), or a lower alcohol such as methanol or ethanol followed by dilution with an aqueous solvent to a concentration of solvent that is biologically compatible with the cells (i.e. not detrimental to the continuing integrity of the cell membrane). Typically the dye is preliminarily dissolved in an organic solvent (preferably DMSO) at a concentration of greater than about 1000-times that used in the staining medium then diluted one or more times into an aqueous medium such as water or a buffer to give a staining solution where the dye is present at a concentration at least sufficient to give a detectable fluorescent signal inside the cells. The staining solution optionally contains additional dyes, such as stains to detect cell viability or fluorescent conjugates of antibodies, avidins, protein A, protein G, or lectins to aid in classification of cell type; nutrients, growth factors, or chelators and preferably does not contain extracellular nucleic acids that may result in background staining or consumption of the staining reagent. Reagents or conditions that temporarily enhance the permeability of materials into cells such as hypotonic medium or detergents may be present if they do not significantly interfere with the biological compatibility of the solution, but are usually not necessary. Preferably the staining solution is completely used within one day and a new staining solution is subsequently prepared.

The optimal concentration of dye in the staining solution depends on the type and concentration of cells in the sample, the type of sample, and the dye itself. The optimal concentration is usually that concentration that results in the optimum fluorescent brightness per cell in the sample. To discriminate two or more types of cells in a mixed population of cells, however, the optimal concentration results in the greatest difference in staining or identifying the various types of cells or parts of cells of interest. In such cases, the optimal concentration does not necessarily yield the greatest intensity of fluorescence or fastest rate of staining. Optimization generally involves two successive steps: 1) determination of cell density, and 2) measurement of the intensity of fluorescence as a function of any variable to be tested such as different dyes, differing dye concentrations, time, temperature, additives to the medium, type of cells or other variables. Analysis of the staining of suspended cells can be conducted either in bulk (e.g. Example 1) using an apparatus such as a fluorometer or a fluorescence plate reader or in an apparatus capable of detecting the staining in single cells such as a flow cytometer (Example 3). The staining of adherent cells that cannot be suspended by trypsinization or other means or for tissues is preferably optimized by a visible observation of a field of cells, such as by viewing the stained cells under a microscope by eye or in conjunction with a solid state camera and imaging software.

The optimal concentration of dye generally depends on the cell density. Bacterial cell density is typically determined from a series of absorption readings taken from a serial dilution of a suspension of cells compared with a duplicate plating of cells on an appropriate solid growth media. The serial dilutions of plated cells are counted and compared with the absorption measurements of the same serial dilutions to determine the relationship between the number of cells or cell forming units per milliliter (cfu/mL) and absorption (cfu/mL/abs). Preferably the readings are taken at cell suspension concentrations between about $1 \times 10^3$ cfu/mL and about $1 \times 10^{10}$ cfu/mL, more preferably between about $1 \times 10^5$ cfu/mL and about $1 \times 10^9$ cfu/mL. Below about $10^3$ cfu/mL, absorption readings are not very reliable. Alternatively, cell densities are determined by direct microscopic count using a standard hemocytometer (particularly for non-bacterial cells). Following determination of cell density, a range of dye concentrations is then used to stain the cell suspensions at different cell densities to determine the optimal dye concentration for the cell density of the sample (Examples 1 and 3). Typically, dye concentrations from about 1 mM down are tested, preferably dye concentrations from about 30 μM down to about 1 μM.

Preferably the 5-DAPP/LIVE dye is present at a concentration sufficient to give a bright red fluorescent emission (i.e. an emission maximum greater than about 540 nm). The concentration of the dye in the staining solution is typically less than about 1 mM; more typically 0.1 μM to 100 μM; most typically about 1 μM to about 30 μM. At very low concentrations of dye (less than about 0.1 μM), the cytosol of eucaryotic cells stains initially with a faint green fluorescence that is only detected with very sensitive instruments such as a microscope equipped with a low light level imaging detector such as an image intensified video camera or an integrating charge-coupled device. The amount of cytoplasmic staining can be limited somewhat by the use of chloroquine to inhibit lysosomal uptake as demonstrated in the pulse and chase technique in Example 10.

The biologically compatible staining solution is combined with a sample containing the cells of interest. Depending on the type of sample and characteristics of the cell population thought to be contained in the sample, the sample is added to the staining solution or the staining solution is added to the sample. For example, a filter containing a retentate removed from a liquid sample can be placed in the aqueous dye solution, allowing the retentate to incubate in the dye solution. Alternatively, where the sample is placed on a slide or in a specialized container, the staining solution can be added to the slide or container before or after the addition of the sample. Usually the staining solution is added to the sample to provide for a relatively homogeneous contact of the sample with the dye for a predetermined length of time. In the case of tissue staining, however, it may not be possible to obtain the desired staining intensity, pattern or discrimination without resorting to a slow perfusion of the dye or topical application.

The cells in the sample are optionally in suspension in a biologically compatible medium or are located on a solid or semisolid support. In one embodiment of the invention, the sample is in suspension on a microscope slide or in a specialized container needed for an instrumentation detection method such as in a cuvette or in a microtiter plate (e.g. 96 well titer plate). Alternatively, the cells in the sample are adhered to a microscope slide or coverslip by normal cellular adhesion or by using an artificial adhesive solution such as poly-L-lysine or are attached to a filter as a retained residue or retentate. Optionally, washing and resuspension of cells are used to further improve the fluorescent response by eliminating background fluorescence.

The living cells in the sample can be obtained from a wide range of sources. In one aspect of the invention, the cells are pure cultures of eucaryotes or procaryotes. Alternatively, the cells are single cell organisms or individual cells or tissues. Similarly, suspensions of cells derived from mechanical/enzymatic dissociation of tissues, adherent tissue culture cells removed from a substrate with Versene, or normally non-adherent cells in culture can be prepared. Generally, the method most universally stains cells that do not have enveloping membranes or multiple layers of polysaccharide beyond the boundary of the plasma membrane. Preferred cells include individual differentiated nucleated animal cells from vertebrates or invertebrates; single-celled organisms such as protozoa; and gram-positive bacteria. Uniformity of staining may be of less concern where it is desired to discriminate between types of cells based on their dye uptake or to visualize staining patterns that may reflect differences in uptake of the dye, such as in tissues or whole organisms.

Although the preferred dyes generally stain all types of living cells, including procaryotes and eucaryotes, plants, animals, fungi, and fungal spores, the dyes are also specifically excluded from certain types of cells. This characteristic allows the dyes to be used to distinguish certain cells from a mixed population of living cells, only some of which exclude the dyes in the method of the invention. Because the low concentrations of dye routinely used in the invention can sometimes give anomalous cytoplasmic staining or may be excluded from certain specific cell types, the optimization of dye and cell concentration, temperature, additives to the medium and changes in other conditions are especially important.

To discriminate two or more types of cells in a mixed population of cells, as in samples of bodily fluids or tissue or testing for contamination, cells can be differentiated based on the intensity or rate of uptake of staining by a 5-DAPP/LIVE dye, optionally in combination with other parameters such as light scatter or intensity of a second dye, to select, quantitate or sort target cells in a mixture of similar or dissimilar cells (e.g. Examples 1,3 and 12). In one aspect of the invention, the 5-DAPP/LIVE dyes are used to identify specific cells in a mixture of blood cells, where there may be questions of both the identity and nucleic acid content of the cell. Alternatively, these dyes are used to discriminate cells by microscopy based on their morphology of staining, relative size or other characteristics in combination with some second parameter such as fluorescence of a second stain or light scattering, as in flow cytometry. Yet another alternative is to use a second fluorescent reagent that is added to the sample, for example, a fluorescent reagent such as fluorescently labeled protein that binds preferentially to cells of interest thought to be contained in the sample (e.g. Example 12).

Typically, it is important to determine which cells in a potentially mixed population of cells are live and which cells are not alive. This is generally done using a second fluorescent dye that is impermeant to living cells, but that stains nucleic acids in a color that contrasts to the generally red color of the 5-DAPP/LIVE dyes (e.g. Examples 1 and 3). If such a measurement is not made, then the relatively rapid staining of dead cells by the 5-DAPP/LIVE dye can potentially be confused with uptake of the 5-DAPP/LIVE dye by live cells. This is particularly necessary where an intensity measurement of cells is made in bulk without observing the fluorescence of single cells or in tissues where there may be several dead cells proximal to where the tissue has been cut.

Suitable dyes for such discrimination are generally nucleic acid stains that are impermeant to live cells and are relatively non-fluorescent when not bound to nucleic acids. Preferably the impermeant stains can be excited at the same or nearly the same wavelength as the 5-DAPP/LIVE dye, but have green or yellow-green fluorescence when bound to the nucleic acid. A variety of suitable dyes are described by pending applications for DIMERS OF UNSYMMETRICAL CYANINE DYES (Ser. No. 07/761,177 filed Sep. 16, 1991 by Yue et al., abandoned), UNSYMMETRICAL CYANINE DYES WITH CATIONIC SIDE CHAIN (Ser. No. 07/833,006 filed Feb. 8, 1992 by Yue, et al., U.S. Pat. No. 5,321,130), and DIMERS OF UNSYMMETRICAL CYANINE DYES CONTAINING PYRIDINIUM MOIETIES (Ser. No. 08/043,665 filed Apr. 5, 1993 by Yue et al.) (all three patent applications incorporated by reference). Examples of suitable dyes with contrasting blue, blue-green, green, yellow-green or yellow fluorescence include dyes commercially available from Molecular Probes, Inc., Eugene, OR under the trademarks PO-PRO-1, POPO-1, BO-PRO-1, BOBO-1, TO-PRO-1, YO-PRO-1, TOTO-1 and YOYO-1. These dyes have the formula:

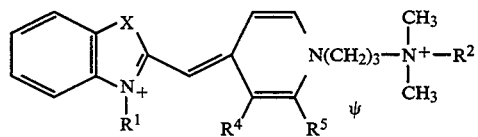

where X is 0 or S; $R^1$ is $C_1$–$C_6$ alkyl, preferably methyl; and $R^2$ is:

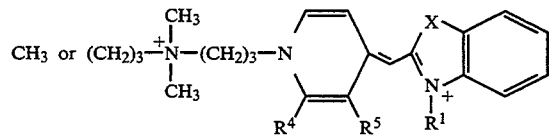

and $R^4$ and $R^5$ are H, in which case the attached heterocyclic ring is a pyridine, or $R^4$ and $R^5$ taken in combination are —CH=CH—CH=CH—, in which case the attached heterocyclic ring is a quinoline.

Alternatively, a second membrane permeant dye such as calcein AM (Molecular Probes, Inc.) can be used to detect viable cells by its conversion to a green-fluorescent product that is retained by viable cells. In this case, only viable cells are stained with a combination of a green fluorescent cytoplasmic stain and the red fluorescent 5-DAPP/LIVE nucleic acid stain and dead cells stain red but do not contain the green fluorescent stain.

In yet another alternative, additional markers, including fluorescent and/or colored dyes, can be added to identify other characteristics of the cells stained with 5-DAPP/LIVE dyes. For example, a labeled protein specific for an external cell marker can be added to distinguish cells containing both the marker and the stained nucleic acids from cells without one or the other. Typically, live nucleated cells can be analyzed this way. First, one staining solution is prepared that contains a 5-DAPP/LIVE phenanthridium dye, where R is a linear alkyl chain containing from 5 to about 8 carbons, where the dye is present at a concentration between about 1 μM and about 25 μM. This concentration is sufficient to give a detectable red fluorescent signal inside living cells of interest. A second biologically compatible staining solution is prepared and added to the sample, either concurrently or sequentially. The second staining solution contains a fluorescent labeled protein that is specific for some aspect of the cells of interest, e.g. an antibody, lectin, protein A or protein G that binds selectively to the cells of interest. Preferably, the second reagent is detectable at a wavelength less than about 540 nm. Nucleated cells can be detected by the presence of both long wavelength and short wavelength fluorescence associated with the same cell.

After the staining solution (preferably an aqueous or mostly aqueous solution containing an optimized dye concentration) is combined with a sample, sufficient time is allowed for the dye in the solution to stain intracellular nucleic acids to give a detectable fluorescent signal inside cells in the sample so that intracellular fluorescence can be evaluated. Generally, less than about 30 minutes is sufficient time for the dye to form a fluorescent dye/nucleic acid complex inside cells in the sample. Typically, the dye solution is combined with the sample for less than about 10 minutes; more typically for about 0.5 minutes to about 5 minutes, although some cells (e.g. lymphocytes) stain almost instantaneously. The differential rate of uptake of the dye into living cells can, in some cases, be used to identify and characterize the cell type in a mixture of cells or in a tissue. In general, staining of living cells with 5-DAPP/LIVE dyes that contain ring substituents such as phenethyl requires longer than staining with 5-DAPP/LIVE dyes in which the substituent is hexyl or octyl. Optimal staining of tissues and cells that have low permeability may require longer incubation periods of up to an hour or more. Where more than one fluorescent reagent is used, the staining solutions are combined with the sample long enough for both dyes to stain the cells or intracellular nucleic acids. In most cases the excess dye, if any, is removed by washing with fresh medium.

Once sufficient time has elapsed for staining the intracellular nucleic acids in the sample, the sample is prepared for observation. The type of preparation depends on the type of sample and the method of observation being utilized. The preparation generally comprises illuminating the sample at a wavelength between about 480 nm and about 550 nm, typically at 480 to about 500 nm. When more than one fluorescent reagent is used the additional dye(s) are excited by light at a wavelength near the absorption maximum of the additional dye(s); preferably between about 320 nm and about 520 nm. The illumination can be accomplished by a light source capable of producing light at or near the wavelength of maximum absorption of the dye, such as an ultraviolet or visible lamp, an arc lamp, a laser, or even sunlight. Preferably the dye is excited by the argon laser at a wavelength equal to about 488 or 514 nm, or by a broad band excitation source between about 480 and 520 nm.

The fluorescent signal of the dye-nucleic acid complex is assayed qualitatively or quantitatively by detection of the resultant light emission at a wavelength of greater than about 540 nm, preferably greater than about 580 nm. The emission is detected by means that include visible inspection, photographic film or electronic imaging, or use of instrumentation such as fluorometers, quantum counters, plate readers, microscopes and flow cytometers, or by means for amplifying the signal such as a photomultiplier. Quantitation of nucleic acid content is determined by comparing the amount of detectable fluorescence with a standard amount of fluorescence for a known amount of nucleic acid. When one or more additional fluorescent reagents are used, the sample is observed with means for separately detecting the red fluorescent signal at a wavelength greater than about 580 nm and of the second fluorescent signal at an appropriate wavelength (e.g. less than about 540 nm).

It is seen from the examples that this series of dyes has several useful characteristics that include, but are not limited to, long wavelength absorption and emission maxima, moderately high affinity for DNA and RNA binding and high fluorescence enhancement on nucleic acid binding. Most importantly, the 5-DAPP/LIVE dyes are superior to ethidium for staining living cells because of their ability to be taken up by a variety of living cells (Examples 1–14). This can be measured qualitatively or quantitatively by several techniques that measure the enhanced fluorescence of the complex, including visual observation, microscopy (Examples 4–10 and 12–13), flow cytometry (Example 3), fluorescence spectroscopy, or analytical fluorometry (Examples 1 and 11).

The short chain versions of the 5-DAPP/LIVE dyes (e.g. group 1 illustrated by butidium) have limited permeability in most cells, depending upon the system being stained, but has a higher binding affinity than the tested longer chain versions (see Table 1 ). In the longer chain versions (group 2 illustrated by hexidium, octidium and phenethidium) there is a marked enhancement of membrane permeability in all systems. Increasing the chain length of a normal alkyl substituent beyond about 6 carbons leads to increased partitioning into membranes and usually to somewhat slower equilibration with nucleic acid-containing compartments such as nuclei. Substitution of ethyl (as in ethidium) by phenethyl (as in phenethidium) facilitates entry of the 5-DAPP dye into living cells, but at a rate that is typically slower than derivatives in which the substituent is a C4 to C8 alkyl group. It is therefore preferred that the substituent R not be too large or too lipophilic; an optimum size of R for n-alkyl groups is pentyl, hexyl or heptyl (especially hexyl) in several types of cells.

TABLE 1

| Dye | $K_p^3$ |
| --- | --- |
| butidium[1] | $9.8 \times 10^6$ |
| hexidium[1] | $8.3 \times 10^6$ |
| octidium[1] | $1.9 \times 10^6$ |
| propidium iodide[2] | $3.8 \times 10^7$ |

TABLE 1-continued

| Dye | $K_p$[3] |
|---|---|
| ethidium iodide[2] | $8.3 \times 10^6$ |

[1]Fluorescence spectra obtained using a standard ratio of 200 μM bp of DNA (bases of RNA) to 1 μM dye (standard solution) in a working buffer (10 mM phosphate, 10% (v/v) ethanol, 1 mM EDTA and 100 mM NaCl), pH 7.4. Fluorescence was measured in a Corning 96 U well plate and Cytofluor ™ 2300 (excitation filter E (560/620), emission filter D (620/640), sensitivity 4) as a function of DNA concentration from 0-100 μM at a constant dye concentration of 0.5 μM.

[2]Fluorescence spectra obtained using the same method as above except the fluorescence was measured in a Cytofluor ™ 2300 (excitation filter E (485/620); excitation D (620/640), and a sensitivity 4) as a function of DNA concentration from 0-30 μM at a constant dye concentration of 0.1 μM.

[3]DNA affinity ($K_p$) determined by linear fitting of plots of reciprocal fluorescence enhancement versus reciprocal DNA concentration, as measured on a microtiter plate fluorescence reader (CytoFluor ™, Millipore).

In some tissue culture cells, the pattern of staining is different from that observed in plant cells or bacteria. In the former case, cells are usually loaded with a brief pulse of dye, followed by a chase of buffered saline solution. These cells show a pattern of staining first in numerous intracellular compartments; e.g. lysosomes. In addition to staining these organelles first, the dyes also undergo a spectral shift to shorter wavelengths when associated with this "early-labeled compartment." If the same cells are exposed to pulses of higher concentrations of the 5-DAPP/LIVE dyes, the staining appears in the mitochondria (tubular structures that are labeled with rhodamine 123) and then, finally, in the nucleus, where it stains the nucleoli very brightly. Nucleoli are the most prominently stained area of higher eukaryotic cells, while the nuclei and cytosol usually stain in a hazy or punctate pattern in these cells. Animal cells loaded to equilibrium with hexidium usually show both intense cytoplasmic and nuclear staining. In plant tissues distinct nuclei tend to label uniformly, but there is frequently significant binding of the dye to cell walls. The plant cells are usually dark except for cell walls and nuclei. The characteristic binding morphology obtained using the 5-DAPP/LIVE dyes thus makes them useful in certain circumstances for identifying the type of cell in a mixed population of cells.

Even the group 2 dyes are not very permeant in some systems, including certain fungal spores, and to a lesser extent, gram negative bacteria. This property confirms the utility of these dyes as differential stains, such as in the differential staining of gram positive and gram negative bacteria in Example 13. When the group 2 dyes are combined with dyes having different spectral properties and specificities (e.g. cell impermeant YOYO-1) they provide very good markers of all cells, including those with intact plasma membranes while the impermeant stain labels only the dead cells. This property is especially useful when attempting to discriminate between live and dead, gram positive and gram negative bacteria (Example 13), but can also be applied to the identification and sorting of fungal spore types, leukocytes, and cells undergoing mitogenic responses to stimulus with lectins, lymphokines, or other biochemical factors; or to detect the presence of excess nucleic acid content in virally-infected cells or those infested with intracellular protozoans such as Plasmodium spp.

In general, as shown in FIG. 1 and in the staining results for several types of cells, ethidium does not enter most live cells easily, butidium enters live cells slowly and is usually not very bright, hexidium enters many types of live cells quickly and is bright and octidium enters cell membranes quickly. Octidium then becomes bright with continued incubation. Phenethidium enters gram positive bacteria but commonly enters tissue culture cells after 1 hr or more. The same trend in staining efficacy is obtained when peripheral blood lymphocytes are loaded with 5-DAPP dyes, but the proportion of the cell occupied by the nucleus is so large that distribution of the dye into this compartment is virtually instantaneous (on the scale of seconds) with butidium, hexidium and octidium, but not ethidium.

EXAMPLE 1

OPTIMIZATION OF LIVE CELL STAINING BASED ON FLUORESCENCE INTENSITY

A culture of Bacillus cereus is washed by centrifugation and resuspended in water to its original volume. Using Corning 96-well microtiter plates with flat bottoms, 150 μL volumes of suspension are loaded per well. A single well of sterile water is the well background standard. Using a Dynatech MR600 microplate reader equipped with a 410 nm filter, absorbance is determined for the initial volumes of suspension. The suspension is diluted by seven serial ten-fold dilutions in water, 150 μL of suspension per well. The absorbance is measured for each dilution. Following the absorbance measurements, each dilution loaded into wells is further diluted 1:10 and plated in duplicate on nutrient growth agar. The colonies are counted and expressed as colony forming units per milliliter (cfu/mL). Using the turbidity of the dilution in the microtiter plate, as described above, the suspension is diluted to a density of about $1 \times 10^7$ cfu/mL.

Using Corning 96-well microtiter flat-bottom plates, a matrix is set up whereby the cell concentration decreases across the plate and the dye concentration decreases down the plate. The top row and first column are reserved for the control, which is sterile water. The bacteria suspension, adjusted to a known density of about $1 \times 10^7$ cfu/mL, as described above, is diluted seven times by serial ten-fold dilutions in water; 150 μL of suspension per well. Three-fold serial dilutions of 5-DAPP/LIVE dye are used (0.14–100 μM) and 10 μM of cell impermeant dead cell marker stain YOYO-1 is added to correct for dead cells. Fifty μL of a solution containing both dyes added at 4× their final concentrations to each well. The final volume per well is 200 μL. The plate is incubated at 25° C. for 30 minutes, then read in a Millipore Cytofluor ™ 2300 96-well fluorescence microplate reader at a fixed excitation of 485±10 nm and emission wavelength of 520±20 nm and 620±20 nm. The high binding affinity of YOYO-1 precludes binding of the 5-DAPP/LIVE dyes to the nucleic acids of bacteria with compromised membranes. The measured intensity per well at 620 nm determines the best dye range and the best cell concentrations (concentrated through the first three ten-fold dilutions) for optimal dye loading while the intensity at 520 nm emission indicates the amount of dead cell staining. Suspensions containing a high percentage (> ~5%) of dead cells are not used in the optimization determination. The data collected allow the determination of optimal dye and cell concentration required for maximal fluorescence intensity per cell.

EXAMPLE 2

MEASURING THE RELATIVE RATE OF UPTAKE OF DYES INTO CELLS

Bacillus cereus is grown in nutrient broth to log phase, washed by centrifugation, and resuspended in water to a density of 5×10⁶ cfu/mL (as determined in Example 1). One centimeter pathlength acrylic cuvettes containing 3 mL of cell suspension are placed in a fluorescence spectrophotometer equipped with a temperature regulated cuvette holder and magnetic stirrer. The suspensions are brought to 23° C. prior to dye addition. To a cuvette of 3 mL bacteria suspension is added 3 μL of 2 mM dye stock solutions in DMSO to give a final dye concentration of 2 μM to produce the maximum attainable fluorescence/cell at the 600 nm emission wavelength (determined as in Example 1). The peak fluorescence excitation and emission wavelengths are determined by scanning the spectrum of the dye in suspensions of Bacillus cereus incubated for 30 min with the dye. Fluorescence intensity of the suspensions is measured using 488 nm excitation and 600 nm emission wavelengths. Sampling of fluorescence is carried out at 5 or 10 Hz until the fluorescence signal appears to stabilize. The results of this measurement are shown in FIG. 1. The figure shows that the rate of dye loading into Bacillus cereus for the linear alkyl derivatives ethidium, butidium, hexidium and octidium increases with carbon chain length, but that the extent of loading is optimal for hexidium.

EXAMPLE 3
OPTIMIZATION OF CELL STAINING BY FLOW CYTOMETRY

Peripheral blood lymphocytes (PBL) are isolated from fresh heparinized goat blood and resuspended to a density of 1×10⁶ cells/mL (as determined by direct microscopic count using a standard hemocytometer) in buffer consisting of 135 mM NaCl, 5 mM KCl, 20 mM HEPES, 1 mM CaCl₂, 1 mM MgCl₂, pH 7.4 (HBSS+). YOYO-1 is added from a 2 mM DMSO stock solution to one mL aliquots of cell suspension to yield a final concentration of 1 μM YOYO-1. The cell suspension is incubated for 5 minutes at room temperature with YOYO-1 before adding enough 5-DAPP/LIVE (fivefold dilutions of the dye ranging in concentration from 20 mM to 2 μM are prepared in DMSO) to yield 1 nM to 10 μM final concentrations of dye with a total of DMSO concentration of 0.1%. Following a 15 minute incubation at room temperature the cells are analyzed in the flow cytometer by exciting both dyes at 488 nm and analyzing both green (YOYO-1) and red (5-DAPP/LIVE) fluorescence. Because of a nearly hundred-fold higher DNA binding affinity of YOYO-1 over 5-DAPP/LIVE and virtual impermeability of YOYO-1 to membranes the cells will fall into two discrete populations with vastly different red/green fluorescence ratios. The optimal concentration for 5-DAPP/LIVE loading of viable cells is that concentration at which maximal staining with 5-DAPP/LIVE is measured.

EXAMPLE 4
STAINING OF MUSHROOM SPORES AS DETECTED BY MICROSCOPY

Spores are rinsed from the gills on the underside of the cap of an agaric using a stream of distilled water. The spores are concentrated by centrifugation for 30 sec at 10,000 rpm in a microcentrifuge then a minimal volume of a 10–20 μM solution of the 5-DAPP/LIVE dye in distilled water is added. The suspension is incubated with the dye for 30 min at room temperature then a 15 μL aliquot of the suspension is mounted on between a coverglass and the slide for viewing in the presence of the dye. The cellular fluorescence is observed on a Zeiss Axioplan fluorescence microscope using fluorescein (long pass emission) or rhodamine filter sets.

The results of staining the spores of mushrooms are variable in that some stain while others do not. Those that are labeled are stained most effectively by hexidium. Ethidium enters less than about 10% of the spores, while butidium stains all spores. With butidium only about 10% of the spores are brightly stained. Hexidium stains all spores brightly while octidium stains only about 10% of them brightly.

EXAMPLE 5
STAINING OF YEAST

Yeast cells are washed by centrifugation and then resuspended in a solution of 2% glucose and 10 mM Na-HEPES, pH 7.4 to a cell density of between 5×10⁵ and 2×10⁶ cells/mL optical density at 410 nm (previously calibrated with YPD agar plate colony counts). Sufficient 10 mM stock solution of the 5-DAPP/LIVE dye in DMSO is added to effect a final concentration of 10 μM of the dye in the medium. The suspension is incubated for 30 min at 37° C. then 15 μL are placed between a coverglass and the microscope slide. The cellular fluorescence is observed using fluorescein (long-pass emission) or rhodamine filter sets.

The staining of Saccharomyces with dyes of different chain lengths varies in distribution and intensity. Ethidium stains all yeast slightly with a pale red nucleus and hazy red cytoplasm. A similar pattern emerges with butidium, but there are more punctate cytoplasmic inclusions stained. Hexidium gives less of a hazy cytoplasmic stain and more distinct nuclei. Although somewhat less bright than hexidium staining, the octidium stains nuclei in somewhat less than 100% of the yeast and has markedly less cytoplasmic staining than any of the other forms.

EXAMPLE 6
STAINING OF PLANT CELL TISSUE

A small section of tissue from the bulb is removed with a razor blade. 0.5 mL of a 10 μM solution of the 5-DAPP/LIVE dye in distilled water is dispensed into a small glass dish. The epidermal tissue is cut into sections and placed in the dye solution. The tissue is stained for 30 min at room temperature in the dark then the tissue preparation is mounted in the presence of the dye between a coverglass and the slide.

Cell walls of Alium spp. stain slightly; more hazy surface staining occurs with ethidium and butidium than with hexidium or octidium. Nuclear staining is evident with all dyes but improves with carbon chain length up to six. Octidium stains identically to hexidium.

EXAMPLE 7
STAINING OF PROTOZOA

1 μL of 10 mM the 5-DAPP/LIVE dye stock is added to 1 mL of protozoan culture. The medium is incubated for 10 min at ambient temperature. 15 μL of this preparation is mounted with dye between a coverglass and the slide. Using this procedure, the nuclei of most cells of the free-living ciliate and flagellate protozoans are stained under these conditions. Hexidium is slightly better than octidium which is better than butidium and ethidium.

EXAMPLE 8

STAINING OF SEA URCHIN SPERM

Sperm cells are released from sea urchins by injection of KCl and the cells are concentrated by low speed centrifugation and suspended in 1 mL artificial seawater (ASW) at room temperature. Sufficient 10 mM dye stock solution is added to the sperm suspension to obtain a final dye concentration of 2 $\mu$M. The sperm are labeled by incubation in the dye solution for 5 min at room temperature. The sperm are washed by centrifugation at 2000 rpm for 1 min and then resuspended in 1 mL ASW before mounting and observation. It is observed that sperm nuclei stain brightly with hexidium. There is no apparent effect on the motility of the sperm or on its ability to fertilize a sea urchin egg.

EXAMPLE 9

STAINING OF NUCLEI IN ADHERENT CULTURED MAMMALIAN CELLS

3T3 mouse fibroblast cells are grown on coverslips in calf serum-supplemented DMEM medium. The coverslips of cells are washed in HBSS+. 5-DAPP/LIVE dye solutions are prepared to a final concentration of 2 $\mu$M in DMEM without serum. One group of 3T3 cells is treated with 300 $\mu$M chloroquine (group 1). These cells and control cells (group 2) not treated with chloroquine are incubated at 37° C. for 30 min. The two groups of cells are transferred to DMEM plus 5-DAPP/LIVE. The cells are incubated in the dye-containing medium for 30 min at room temperature and are subsequently washed in HBSS+ and viewed by epifluorescence microscopy using a long-pass fluorescein or a rhodamine filter set.

After one half hour, the nucleus and cytoplasm of cells stained with butidium, hexidium or octidium appeared orange when viewed through the long-pass fluorescein filter (red with rhodamine excitation). Control cells (group 2) have relatively equal staining in the nucleus and cytoplasm and punctate staining-in the latter area. This is seen as tube-shaped regions; morphologically most similar to mitochondria. Cells treated with chloroquine are also stained throughout, but with a greater relative intensity of staining in the nucleus. Cytoplasmic fluorescence is less punctate than that seen in the control cells and fewer "tubular" bodies are seen.

EXAMPLE 10

PULSE-CHASE STAINING OF LYSOSOMAL COMPARTMENTS IN CULTURED MAMMALIAN CELLS

3T3 mouse fibroblast cells are grown on coverslips in calf serum-supplemented DMEM medium. The coverslips of cells are washed using the HBSS+, then hexidium solutions are prepared to final concentrations of 2 $\mu$M and 0.2 $\mu$M in HBSS+. The cells are incubated in the dye-containing medium for 2 min at room temperature then they are washed in HBSS +and viewed by epifluorescence microscopy using a long-pass fluorescein or a rhodamine filter set.

Brief pulse-chase loading of 3T3 cells with 0.2 $\mu$M hexidium results in labeling of punctate structures in the cell cytoplasm. Fluorescence from these structures appears green. Preincubation of the cells with 300 $\mu$M chloroquine reduces the amount of cytoplasmic staining. Loading with 2 $\mu$M hexidium for the same length of time results in additional organellar staining, which is apparently mitochondrial. Under both of these conditions nuclei are stained slightly, but only in the nucleolar regions.

EXAMPLE 11

STAINING OF LYMPHOCYTES

Peripheral blood lymphocytes (PBL) are isolated from fresh heparinized goat blood and resuspended in buffer consisting of 135 mM NaCl, 5 mM KCl, 20 mM HEPES, 1 mM CaCl$_2$, 1 mM MgCl$_2$, pH 7.4 (HBSS+). The cells are resuspended to $10^6$mL (as determined by direct microscopic count using a standard hemocytometer) in a final volume of 3 mL in the above buffer in a quartz cuvette. 5-DAPP/LIVE dye stocks are prepared to final concentrations of 2 mM in DMSO. 3 $\mu$L of the octidium dye stock solution is injected into the cuvette to a final concentration of 2 $\mu$M. In a fluorometer, the sample is excited at 520 nm and fluorescence emission is monitored at 600 nm over the time required for the fluorescence signal to become stable. Hexidium, butidium and ethidium bromide are injected into separate samples of PBL to determine the relative rates of uptake for these stains. The volume of dye solution added to the cuvette is corrected by a factor relating the absorbance of the dye to the absorbance of a 2 mM octidium solution.

With all indicators except ethidium bromide, a rapid increase in fluorescence is seen that reaches a stable level almost instantaneously. Ethidium bromide shows essentially no increase in fluorescence signal over time.

EXAMPLE 12

COMPARISON OF TWO DIFFERENT CELL POPULATIONS USING TWO FLUORESCENT DYES

The relative size of populations of bacteria in milk containing *Streptococcus lactis* and *Salmonella typhimurium* is determined by fluorescence microscopy after exposing the bacteria to 2 $\mu$M hexidium in combination with 1 $\mu$g/ml AMCA-IgG directed against Salmonella. The AMCA labeled IgG is prepared according to Brinkley, BIOCONJ. CHEM, 3, 1-13 (1992). Rabbit IgG is dissolved at 5-10 mg/mL in 50-100 mM sodium bicarbonate buffer pH about 8.2 at room temperature. AMCA dye in a sufficient amount from a stock solution is added to contain 0.25 mg of succinimidyl ester for each 10 mg of antibody. The solution of reactive AMCA dye should be added dropwise during a period of about 1 minute, using a Hamilton syringe (or equivalent) to the antibody solution with stirring while in an ice bath. The solution is allowed to warm to room temperature and is stirred for exactly two hours. The conjugate is separated from the unreacted dye on a Sephadex G-25 gel filtration column using an appropriate buffer and determine the degree of substitution of the conjugate by the procedure described in Brinkley, BIOCONJ. CHEM. 3, 1-13, (1992).

Both dyes are prepared by dilution of 1 mM DMSO stock solutions in water. This combination allows detection of all bacteria, but Streptococci appear orange-red while Salmonella have a distinct blue halo when both are excited at 360 nm and observed with a 440 nm long-pass barrier filter.

EXAMPLE 13

STAINING FOLLOWED BY FIXATION

Adherent rainbow trout gonad cells (RTG-2) are grown at 20° C. until about 25% confluent. The cells are labeled by incubation in HBSS- containing 1 μM hexidium at room temperature for 30 min. The cells are subsequently washed free of hexidium with HBSS-, followed by phosphate-buffered saline, pH 7.4 (PBS), and fixed in 2% formaldehyde in PBS for 15 min at room temperature. Cell nuclei and cytoplasmic fluorescence are observed in the fluorescence microscope using fluorescein long-pass or rhodamine filter sets. There is essentially no difference between live cells loaded to equilibrium with 1 μM hexidium and cells loaded with the same concentration of hexidium and fixed with 2% formaldehyde.

It is to be understood that, while the foregoing invention has been described in detail by way of illustration and example, numerous modifications, substitutions, and alterations are possible without departing from the spirit and scope of the invention as described in the following claims.

What is claimed is:

1. A method of detecting nucleic acids in living mammalian or bacterial cells comprising:
    a) preparing a biologically compatible staining solution comprising a phenanthridium dye of the formula:

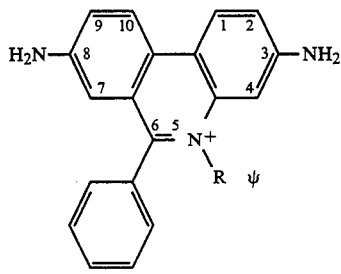

where R is a hydrocarbon substituent that contains from 4 to about 10 carbons and is optionally saturated or unsaturated, and is linear or branched or contains an alicyclic or aromatic ring, and the symbol Ψ depicts the presence of the counterion used to neutralize the positive charge on the dye; where said dye is present at a concentration sufficient to give a detectable fluorescent signal inside living cells of interest; and
    b) combining the staining solution with a sample containing the living cells of interest;
    c) preparing the sample for observation by illuminating the sample with a light source capable of producing a light at or near the wavelength of maximum absorption of the dye; and
    d) observing the sample with means for detecting the fluorescent signal.

2. A method, as claimed in claim 1, for measuring the amount of nucleic acids in living cells, further comprising: comparing the amount of detectable fluorescence with a standard amount of fluorescence for a known amount of nucleic acid.

3. A method, as claimed in claim 1, further comprising adding to the sample a second fluorescent dye to detect the presence of cells in which the membrane is not intact.

4. A method, as claimed in claim 1, further comprising: sorting cells based on the amount of fluorescent signal per cell.

5. A method, as claimed in claim 1, where the R substituent of the phenanthridium dye is a $C_{5-8}$ alkyl chain that is linear or branched.

6. A method, as claimed in claim 1, where the phenanthridium dye is hexidium.

7. A method, as claimed in claim 1, where the phenanthridium dye is present at a concentration less than 100 μM.

8. A method, as claimed in claim 1, where the phenanthridium dye is present at a concentration between 1 μM and 25 μM.

9. A method, as claimed in claim 1, where the sample is combined with the staining solution for 30 minutes or less.

10. A method, as claimed in claim 1, where the sample is observed with a laser scanner, a flow cytometer, a fluorescence microscope, or a confocal microscope.

11. A method, as claimed in claim 1, where the sample contains blood cells.

12. A method, as claimed in claim 1, where the sample contains mammalian cells.

13. A method, as claimed in claim 1, where the sample contains Gram positive bacteria cells.

14. A method, as claimed in claim 1, where preparing the sample for observation comprises illuminating the sample with a wavelength between about 480 nm and about 520 nm.

15. A method, as claimed in claim 14, where preparing the cells for observation further comprises fixing the cells prior to illumination.

16. A method for analyzing live nucleated mammalian cells comprising:
    a) preparing a first biologically compatible staining solution comprising a first reagent that is a phenanthridium dye of the formula:

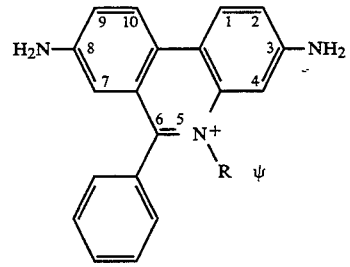

where R is a linear alkyl chain containing from 5 to 8 carbons, and the symbol Ψ depicts the presence of the counterion used to neutralize the positive charge on the dye; where said dye is present at a concentration between 1 μM and 25 μM that is sufficient to give a detectable red fluorescent signal inside living cells of interest
    b) combining the first staining solution with a sample containing the living nucleated cells of interest for a sufficient time for the first reagent to stain intracellular nucleic acids to give the detectable red fluorescent signal;
    c) preparing a second biologically compatible staining solution comprising a second reagent that is a fluorescent labeled protein that is an antibody, lectin, protein A or protein G that binds selectively to the cell of interest and is detectable at a wavelength less than about 540 nm;

d) combining the second staining solution with the sample for a sufficient time for the second reagent to stain the cells to give a second fluorescent signal that is separately detectable from the red fluorescent signal;

e) preparing the sample for observation by illuminating the sample with a light source capable of producing a light at or near the wavelength of maximum absorption of the first and second reagents; and f) observing the sample with means for separately detecting the red fluorescent signal at a wavelength greater than about 580 nm and of the second fluorescent signal at a wavelength less than about 540 nm.

17. A method of detecting nucleic acids in living mammalian cells comprising:

a) preparing a biologically compatible staining solution comprising a phenanthridium dye of the formula:

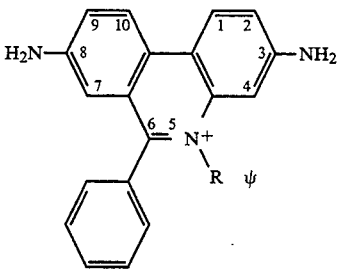

where R is a linear alkyl chain containing from 5 to 8 carbons, and the symbol Ψ depicts the presence of the counterion used to neutralize the positive charge on the dye; where said dye is present at a concentration between 1 μM and 25 uM that is sufficient to give a detectable fluorescent signal inside living cells of interest; and b) combining the staining solution with a sample containing the living mammalian cells of interest for a sufficient time for the dye to stain intracellular nucleic acids to give the detectable fluorescent signal;

c) illuminating the sample with a wavelength between about 480 nm and about 520 nm; and d) observing the sample with an instrument for detecting the fluorescent signal.

18. A method, as claimed in claim 17, where the fluorescent signal is detected by a flow cytometer.

19. A method, as claimed in claim 17, where the fluorescent signal is detected by a microscope.

20. A method, as claimed in claim 17, further comprising: adding to the sample a second fluorescent reagent.

* * * * *